US006218563B1

(12) United States Patent
Lennon et al.

(10) Patent No.: US 6,218,563 B1
(45) Date of Patent: Apr. 17, 2001

(54) CYANOPHOSPHONAMIDES AND METHOD FOR PREPARATION

(75) Inventors: Patrick J. Lennon, Webster Groves; Serge G. Vulfson, Chesterfield, both of MO (US)

(73) Assignee: Monsanto Company, St. Louis, MO (US)

( * ) Notice: Subject to any disclaimer, the term of this patent is extended or adjusted under 35 U.S.C. 154(b) by 0 days.

(21) Appl. No.: 09/450,309

(22) Filed: Nov. 29, 1999

Related U.S. Application Data
(60) Provisional application No. 60/110,792, filed on Dec. 3, 1998.

(51) Int. Cl.[7] .................................. C07F 9/02; C07F 9/22
(52) U.S. Cl. ........................... 558/138; 558/145; 562/10; 562/877
(58) Field of Search .................................. 558/138, 145; 562/10, 11, 877

(56) References Cited

U.S. PATENT DOCUMENTS

| | | | |
|---|---|---|---|
| 2,402,703 | 6/1946 | Woodstock | 260/461 |
| 2,702,299 | 2/1955 | Harris | 260/461 |
| 3,432,277 | 3/1969 | Roesky | 23/357 |
| 3,812,221 | 5/1974 | Braden et al. | 260/968 |
| 4,221,583 | 9/1980 | Gaertner et al. | 71/86 |
| 4,568,432 | 2/1986 | Rogers | 204/73 |
| 4,634,705 | 1/1987 | DeBernardis et al. | 514/256 |
| 5,688,965 | 11/1997 | Kim et al. | 548/452 |

FOREIGN PATENT DOCUMENTS

| | | | |
|---|---|---|---|
| 767511 | 7/1952 | (DE) . | |
| 300 936 | 9/1992 | (DE) | C07F/9/40 |
| 96/15135 | 5/1996 | (WO) | C07F/9/38 |

OTHER PUBLICATIONS

Albrecht et al., "Reaction of the Two–Component System Trialkyl Phosphite/Carbon Tetrachloride with Nucleophiles 3. Reaction in Presence of Trialkylammonium Salts," *Z. anorg. allg. Chem.* 552: 132–146 (1987) and English language translation.

Kashemirov et al., "Troika Acids: Synthesis, Structure, and Fragmentation Pathways of Novel α–(Hydroxyimino)phosphonacetic Acids," *J. Am. Chem. Soc.* 117: 7285–7286 (1995).

Shioiri et al., "Reaction of Diethyl Phosphorocyanidate(DEPC) with Carboxylic Acids. A New Synthesis of Carboxylic Esters and Amides," *Tetrahedron* 32(18): 2211–2217 (1976).

Tung et al., "A New Method for the Preparation of O,O'–Dialkylphosphoryl Cyanides," *Hua Hsueh Hsueh Pao (Acta Chimica Sinica)* 31(3): 199–202 (1965).

Abstract—Database WPI, Section Ch, Week 7615, Derwent Publications Ltd., London, GB; AN 76–27192X, XP002061354 & JP 51 023 225 A (Nippon Chem. Ind. Co. Ltd.), Feb. 24, 1976.

Blanchard, J. "Préparation d–acides beta–amino–ethyl–phosphoniques" *Tetrahedron*, vol. 32, No. 4, 1976, Oxford GB, pp. 455–459, XP002061374.

Chemical Abstracts, vol. 093, No. 12, Sep. 22, 1980, Columbus, Ohio, US; abstract No. 123612, Zhurba, Y.I. et al. "Increase in the stability of silver complexes in the process of simultaneous developing and fixing" and Zh Nauchn, Pirkl. Fotogr. Kinematogr.(ZNPFAG, 00444561); 80; vol. 25(3); pp. 182–185, Vses. Gos. Nauchno–Issled. Proektn. Inst. Khim.–Fotogr. Prom., Moscow; USSR; XP002061352.

Dyatkina, N. et al. Synthesis and antiviral activity of some fluorinated nucleotide derivativers: Nucleosides Nucleotides (NUNUD5, 07328311); 94; col. 13 (1–3); pp. 325–337, Engelhardt Inst. Mol. Biol.; Mowcow; 117984, Russia XP002061348.

Kashemirov, B.A. "(E)–(Hydroxyimino)(hydroxymethoxyphosphinyl)acetic acid: Synthesis and pH dependent fragmentation," *Tetrahedron Letters*, vol. 36, No. 52, 1995, Oxford GB, pp. 9437–9440; XP002061351.

Brodskii et al. "Identification and Determination of Chemical Warfare Components and Their Decomposition Products Using Mass Chromatograms in Characteristic Ions and in Ion Mass Differences". Journal of Analytical Chemistry. vol. 52, No. 8, 1997, pp 801.*

\* cited by examiner

*Primary Examiner*—Floyd D. Higel
*Assistant Examiner*—Ebenezer Sackey
(74) *Attorney, Agent, or Firm*—Ira D. Finkelstein; Howrey Simon Arnold & White, LLP

(57) ABSTRACT

The present invention provides a process for preparing a cyanophosphonamide comprising contacting phosphoric anhydride and a cyanide, preferably in the presence of a Lewis base, to produce a cyanophosphonate intermediate, and subsequently contacting the cyanophosphonate intermediate with an amino compound.

48 Claims, No Drawings

CYANOPHOSPHONAMIDES AND METHOD FOR PREPARATION

This application claims benefit form provisional application 60/110,792 filed Dec. 3, 1998.

BACKGROUND OF THE INVENTION

1. Field of the Invention

The present invention relates generally to cyanophosphon method for their preparation.

2. Description of Related Art

Organophosphorus compounds have numerous and varied applications, for example, in herbicides, insecticides, fertilizers, flame retardants and plasticizers and as precursors for the synthesis of other organophosphorus compounds. Cyanophosphonates and their derivatives, as well as salts thereof, are of particular interest due to their versatility in synthetic pathways, and a wide range of chemistries may extend from both the phosphorus and cyano moieties. For example, cyanophosphonate derivatives may be converted to aminomethylphosphonate derivatives, which have been particularly important precursors in the synthesis of N-phosphonomethylglycine, commonly known as glyphosate, a highly effective commercial herbicide (available under the trade name ROUNDUP®) useful for the control of a large variety of weeds.

There is a need in the art for alternative processes for preparing cyanophosphonate derivatives to be used in the synthesis of amino phosphonate compounds. It is desirable for such derivatives to include a wide range of primary and secondary amine derivatives in order to provide a broad basis for further chemistry. It is also desirable for the derivatives to be isolable as the monoacid or as a salt. There is a further need for such novel processes that are economical and environmentally safe.

SUMMARY OF THE INVENTION

The present invention provides a process for preparing a cyanooxyphosphorus compounds comprising contacting phosphoric anhydride and a cyanide, preferably in the presence of a Lewis base, to produce a cyanophosphonate intermediate, and subsequently contacting the cyanophosphonate intermediate with an amino compound. The amino compound is preferably an aliphatic or aromatic primary or secondary amine, or an amino acid derivative. The cyanooxyphosphorus compounds produced in the process of the present invention can further be used to produce other organophosphorous compounds, such as aminomethylphosphonates or N-phosphonomethylglycine.

The processes and compositions according to the invention offer significant advantages in that they provide a novel, economic route to synthesize cyanophosphonate derivatives and other cyanooxyphosphorus compounds having improved environmental impact over conventional processes using halogen-containing phosphorus starting materials.

DESCRIPTION OF ILLUSTRATIVE EMBODIMENTS

The invention is broadly directed to a process that involves contacting phosphoric anhydride ($P_4O_{10}$) and a cyanide, preferably in the presence of a Lewis base, in a reaction mixture under conditions to produce a cyanooxyphosphorous compound. The step of contacting phosphoric anhydride and a cyanide can produce a variety of cyanooxyphosphorus compounds, herein defined as compounds comprising an —O—P—CN moiety. Examples of cyanooxyphosphorous compounds include cyanophosphonates, dicyanophosphinates, dicyanopyrophosphonates, dicyanotripolyphosphates, monocyanopyrophosphates, monocyanopolyphosphates, and dicyanopolyphosphates. A preferred cyanooxyphosphorous compound is cyanophosphonate or a cyanophosphonate derivative. The cyanooxyphosphorous compound, e.g. cyanophosphonate derivative, is subsequently contacted with an amino compound to produce a cyanophosphonamide.

In another embodiment, the invention is directed to a process that involves contacting the cyanooxyphosphorous compound with an amino compound to produce a cyanooxyphosphonamide. The cyanooxyphosphorous compound can be provided by the method described above or by any other method known to the skilled artisan.

Cyanophosphonamides of the present invention can be generally represented by the following formula:

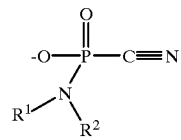

wherein $R^1$ and $R^2$ are determined by the amino compound used, as set forth herein.

For example, the inventive process may involve charging a reaction vessel with one equivalent of phosphoric anhydride, optionally with a nonreactive, polar solvent. A Lewis base is then added, preferably in an amount ranging from about 1 to about 10 molar equivalents relative to phosphoric anhydride, more preferably about 2 to about 8 molar equivalents, and most preferably about 3 to about 6 molar equivalents. That mixture is then heated under suitable conditions to dissolve or partially dissolve the phosphoric anhydride, e.g., preferably at a temperature of about 40° C. and for about 10 minutes.

Subsequently, a cyanide compound is added, preferably in an amount ranging from about 1 to about 15 molar equivalents relative to phosphoric anhydride, more preferably about 2 to about 10 molar equivalents and most preferably about 3.5 to about 8.5 molar equivalents. This mixture is then heated under suitable conditions to carry out the reaction. The reaction temperature is preferably between about 0° C. and about 150° C., and more preferably between about 30° C. and about 90° C. The reaction time preferably ranges from about 0.5 to about 50 hours, more preferably from about 1 to about 20 hours and most preferably from about 1 to about 6 hours. The Lewis base and any solvent can subsequently be removed from the product mixture, for example, under reduced pressure. An amino compound is then added to the remaining residue to produce the cyanophosphonamide. The amount of the amino compound added is generally between about 0.2 and 20 equivalents, preferably between about 0.9 and 5 equivalents. The temperature of the contacting is preferably between about 0° C. and 80° C., and more preferably between about 20° C. and 50° C. The reaction time of the contacting preferably ranges from about 1 to about 100 hours, more preferably from about 2 to about 20 hours.

Phosphoric anhydride is available in high purity, for example, from Aldrich Chemical Co. in purities in excess of 99.99%. The phosphoric anhydride is generally available in the form of a powder and may be added to the reaction mixture in various forms. For example, phosphoric anhydride can be added directly as a powder or as a slurry in a solvent or cosolvent, such as acetonitrile, propionitrile, adiponitrile, benzylcyanide, and sulfolane.

The cyanide compound can be hydrogen cyanide or a cyanide salt that is sufficiently reactive with phosphoric anhydride to produce a cyanophosphorus compound. For example, the cyanide compound can be an alkali metal cyanide, an alkaline earth metal cyanide, a Group IB metal cyanide, an ammonium cyanide, a tetraalkyl ammonium cyanide, a tetraalkyl phosphonium cyanide, a trialkyl sulfonium cyanide, a cyanide of a cationic form of an organic amine, or mixtures thereof. The cyanide compound is preferably hydrogen cyanide, calcium cyanide, potassium cyanide, sodium cyanide, lithium cyanide, silver cyanide, gold cyanide, copper cyanide, tetrabutylammonium cyanide or mixtures thereof. More preferably, the cyanide compound is potassium cyanide, sodium cyanide, tetrabutylammonium cyanide or mixtures thereof.

The Lewis base is generally any base suitable for promoting the production of the desired compounds according to the invention. Preferably, the Lewis base is a tertiary amine Lewis base, such as triethylamine, trimethylamine, 4-tert-butylpyridine, or quinuclidine, or mixtures thereof. More preferably, the Lewis base is 4-tert-butylpyridine or quinuclidine. The Lewis base can be added to the reaction mixture in an amount ranging from about 1 to about 10 molar equivalents, more preferably from 2 to about 8 molar equivalents and most preferably from 3 to about 6 molar equivalents.

The solvent can be any material which enhances the solubility of the reactants or promotes the formation of the desired products. For the step of reacting phosphoric anhydride and a cyanide, preferably the solvent is a polar aprotic solvent, for example, a nitrile such as acetonitrile, benzylcyanide, adiponitrile, propionitrile, dimethylacetonitrile, sulfolane, or mixtures thereof. More preferably, the solvent is acetonitrile, benzylcyanide, adiponitrile, or sulfolane.

For the step of reacting a cyanooxyphosphorous compound with an amino compound, preferably the solvent is an aprotic solvent, and more preferably the solvent is an aprotic polar solvent. Most preferably, the solvent is selected from the group consisting of amides, ethers, sulfoxides, esters, and nitriles.

Amino compounds useful in the process of the present invention include primary and secondary amines, or alkali metal salts thereof, and amino acid derivatives. Preferably, the amino compound is an aliphatic or aromatic primary or secondary amine. Additionally, in the process of the present invention, hydrazines, and di- and poly-amines can be used as reactants, either in equimolar amounts or in amounts so as to prepare two or more cyanophosphonamides on the same molecule.

The primary amine can be a straight chain or branched alkyl amine, an arylamine, an arylalkylamine, a cycloalkyl amine, a polycycloalkyl amine, or mixtures thereof. Examples of straight chain alkyl amines include methylamine, ethylamine, 1-propylamine, 1-butylamine, 1-pentylamine, 1-hexylamine, 1-heptylamine, 1-octylamine, 1-decylamine, 1-dodecylamine, 1-tetradecylamine and 1-hexadecylamine. Examples of branched chain alkyl amines include 2-aminopropane, 2-aminobutane, 2-methyl-2-aminopropane, 2-methyl-1-aminopropane, 2-aminopentane, 3-aminopentane, 3-methyl-1-aminobutane, 2,2-dimethylaminopropane, 3-methyl-2-aminobutane, 1,1 dimethylaminopropane, 2-methyl-1-aminobutane, 1-methyl-1-aminobutane, 4-methyl-1-aminopentane, 3-methyl-1-aminopentane, 2-methyl-1-aminopentane, 1-methyl-1-aminopentane, 3,3-dimethyl-1-aminobutane, 2,3-dimethyl-1-aminobutane, 2,4-dimethyl-1-aminobutane, 1,2-dimethyl-1-aminobutane, 2,2-dimethyl-1-aminobutane, 1,1-dimethyl-1-aminobutane, 1,1,2-trimethylaminopropane, 3-methyl-3-aminopentane, 2-ethyl-1-aminobutane, 2-ethyl-1-aminobutane, 2-heptylamine, and 2-octylamine.

Arylamines include aniline, o-toluidine, m-toluidine, p-toluidine, 2,3-xylidine, 2,4-xylidine, 2,5-xylidine, 2,6-xylidine, 3,4-xylidine, 3,5-xylidine, o-nitroaniline, m-nitroaniline, p-nitroaniline, benzidine, o-tolidine, o-phenylenediamine, m-phenylenediamine, and p-phenylenediamine. Examples of arylalkylamine are benzylamine and β-phenylethylamine. Cycloalkylamines useful in the present invention include cyclobutylamine, cyclopentylaamine, cyclohexylamine, cycloheptylaamine, and cyclooctylamine. Examples of polycycloalkylamine include 1-aminodecalin, 2-aminodecalin, 1-aminotetralin, 2-aminotetralin, 1-adamantamine, and 2-adamantanamine.

Examples of secondary amine useful in the process of the present invention include dimethylamine, diethylamine, dipropylamine, diisopropylamine, dibutylamine, dihexylamine, diphenylamine, dibenzylamine, methylethylamine, di(2-methoxyethyl) amine, ditridecylaamine, N-methylaniline, N-ethylaniline, N-methylcyclohexylamine, and N-ethylcyclohexylamine.

As previously mentioned, alkali metal salts of primary and secondary amines can also be used in the process of the present invention. The alkali metal is preferably sodium, potassium, or lithium, and more preferably, lithium.

The amino acid derivative can be a natural or unnatural amino acid, a salt of an amino acid, an ester of an amino acid, or an amide of an amino acid. If an amino acid or amino acid is isoelectric or protonated, it is desirable that a base is additionally present.

Examples of natural amino acids include L-alanine, L-aspartic acid, L-glutamic acid, L-phenylalanine, glycine, L-isoleucine, L-lysine, L-leucine, L-methionine, L-asparagine, L-proline, L-glutamine, L-arginine, L-valine, L-tryptophan, β-alanine, isoglutamine, norleucine, norvaline, omithine, penicillamine, pyroglutamic acid, sarcosine, statine, p-aminobenzoic acid, and γ-aminobutyric acid. Unnatural amino acids useful in the present invention include D-alanine, D-aspartic acid, D-glutamic acid, D-phenylalanine, D-isoleucine, D-lysine, D-leucine, D-methionine, D-asparagine, D-proline, D-glutamine, D-arginine, D-valine, D-tryptophan, hydroxyethylcysteine, trans-3-methylproline, iminodiacetic acid, homoglutamine, nitroglutamine, allo-threonine, α,α,α-trifluoroalanine, and pipecolic acid.

The salt of an amino acid is preferably a sodium salt of an amino acid or a potassium salt of an amino acid. Examples of salts of amino acids include alanine sodium salt, aspartic acid sodium salt, glutamic acid sodium salt, phenylalanine sodium salt, glycine sodium salt, histidine sodium salt, isoleucine sodium salt, lysine sodium salt, leucine sodium salt, methionine sodium salt, asparagine sodium salt, proline sodium salt, glutamine sodium salt, arginine sodium salt, valine sodium salt, tryptophan sodium salt, sarcosine sodium salt, γ-aminobutyric acid sodium salt, iminodiacetic acid sodium salt, alanine potassium salt, aspartic acid potassium salt, glutamic acid potassium salt, phenylalanine potassium salt, glycine potassium salt, histidine potassium salt, isoleucine potassium salt, lysine potassium salt, leucine potassium salt, methionine potassium salt, asparagine potassium salt, proline potassium salt, glutamine potassium salt, arginine potassium salt, valine potassium salt, tryptophan potassium salt, sarcosine potassium salt, iminodiacetic acid potassium salt, and γ-aminobutyric acid potassium salt.

The ester of an amino acid is preferably an alkyl ester, an aryl ester, or an arylalkyl ester. Examples of alkyl esters of amino acids are alanine methyl ester, aspartic acid methyl ester, aspartic acid dimethyl diester, glutamic acid methyl ester, glutamic acid dimethyl diester, phenylalanine methyl ester, glycine methyl ester, histidine methyl ester, isoleucine methyl ester, lysine methyl ester, leucine methyl ester, methionine methyl ester, asparagine methyl ester, proline methyl ester, glutamine methyl ester, arginine methyl ester, valine methyl ester, tryptophan methyl ester, sarcosine methyl ester, iminodiacetic acid dimethyl ester, alanine ethyl ester, aspartic acid ethyl ester, aspartic acid diethyl diester, glutamic acid ethyl ester, glutamic acid diethyl diester, phenylalanine ethyl ester, histidine ethyl ester, isoleucine ethyl ester, lysine ethyl ester, leucine ethyl ester, methionine ethyl ester, asparagine ethyl ester, proline ethyl ester, glutamine ethyl ester, arginine ethyl ester, valine ethyl ester, tryptophan ethyl ester, sarcosine ethyl ester, iminodiacetic acid diethyl ester, alanine t-butyl ester, aspartic acid t-butyl ester, aspartic acid di-t-butyl diester, glutamic acid t-butyl ester, glutamic acid di-t-butyl diester, phenylalanine t-butyl ester, glycine t-butyl ester, histidine t-butyl ester, isoleucine t-butyl ester, lysine t-butyl ester, leucine t-butyl ester, methionine t-butyl ester, asparagine t-butyl ester, proline t-butyl ester, glutamine t-butyl ester, arginine t-butyl ester, valine t-butyl ester, tryptophan t-butyl ester, sarcosine t-butyl ester, sarcosine t-butyl ester, iminodiacetic acid di-t-butyl ester, alanine isopropyl ester, aspartic acid isopropyl ester, aspartic acid diisopropyl diester, glutamic acid isopropyl ester, glutamic acid diisopropyl diester, phenylalanine isopropyl ester, glycine isopropyl ester, histidine isopropyl ester, isoleucine isopropyl ester, lysine isopropyl ester, leucine isopropyl ester, methionine isopropyl ester, asparagine isopropyl ester, proline isopropyl ester, glutamine isopropyl ester, arginine isopropyl ester, valine isopropyl ester, tryptophan isopropyl ester, sarcosine isopropyl ester, iminodiacetic acid diisopropyl ester, alanine cyclohexyl ester, aspartic acid cyclohexyl ester, aspartic acid dicyclohexyl diester, glutamic acid cyclohexyl ester, glutamic acid dicyclohexyl diester, phenylalanine cyclohexyl ester, glycine cyclohexyl ester, histidine cyclohexyl ester, isoleucine cyclohexyl ester, lysine cyclohexyl ester, leucine cyclohexyl ester, methionine cyclohexyl ester, asparagine cyclohexyl ester, proline cyclohexyl ester, glutamine cyclohexyl ester, arginine cyclohexyl ester, valine cyclohexyl ester, tryptophan cyclohexyl ester, sarcosine cyclohexyl ester, iminodiacetic acid dicyclohexyl ester, alanine dodecyl ester, aspartic acid dodecyl ester, aspartic acid didodecyl diester, glutamic acid dodecyl ester, glutamic acid didodecyl diester, phenylalanine dodecyl ester, glycine dodecyl ester, histidine dodecyl ester, isoleucine dodecyl ester, lysine dodecyl ester, leucine dodecyl ester, methionine dodecyl ester, asparagine dodecyl ester, proline dodecyl ester, glutamine dodecyl ester, arginine dodecyl ester, valine dodecyl ester, tryptophan dodecyl ester, sarcosine dodecyl ester, iminodiacetic acid didodecyl ester, alanine hexadecyl ester, aspartic acid hexadecyl ester, aspartic acid dihexadecyl diester, glutamic acid hexadecyl ester, glutamic acid dihexadecyl diester, phenylalanine hexadecyl ester, glycine hexadecyl ester, histidine hexadecyl ester, isoleucine hexadecyl ester, lysine hexadecyl ester, leucine hexadecyl ester, methionine hexadecyl ester, asparagine hexadecyl ester, proline hexadecyl ester, glutamine hexadecyl ester, arginine hexadecyl ester, valine hexadecyl ester, tryptophan hexadecyl ester, sarcosine hexadecyl ester, iminodiacetic acid dihexadecyl ester, alanine octadecyl ester, aspartic acid octadecyl ester, aspartic acid dioctadecyl diester, glutamic acid octadecyl ester, glutamic acid dioctadecyl diester, phenylalanine octadecyl ester, glycine octadecyl ester, histidine octadecyl ester, isoleucine octadecyl ester, lysine octadecyl ester, leucine octadecyl ester, methionine octadecyl ester, asparagine octadecyl ester, proline octadecyl ester, glutamine octadecyl ester, arginine octadecyl ester, valine octadecyl ester, tryptophan octadecyl ester, sarcosine octadecyl ester, and iminodiacetic acid dioctadecyl diester.

Examples of arylalkyl esters of amino acids useful in the present invention are alanine benzyl ester, aspartic acid benzyl ester, aspartic acid dibenzyl diester, glutamic acid benzyl ester, glutamic acid dibenzyl diester, phenylalanine benzyl ester, glycine benzyl ester, histidine benzyl ester, isoleucine benzyl ester, lysine benzyl ester, leucine benzyl ester, methionine benzyl ester, asparagine benzyl ester, proline benzyl ester, glutamine benzyl ester, arginine benzyl ester, valine benzyl ester, tryptophan benzyl ester, and sarcosine benzyl ester. Aryl esters of amino acids useful in the present invention include alanine phenyl ester, aspartic acid phenyl ester, aspartic acid diphenyl diester, glutamic acid phenyl ester, glutamic acid diphenyl diester, phenylalanine phenyl ester, glycine phenyl ester, histidine phenyl ester, isoleucine phenyl ester, lysine phenyl ester, leucine phenyl ester, methionine phenyl ester, asparagine phenyl ester, proline phenyl ester, glutamine phenyl ester, arginine phenyl ester, valine phenyl ester, tryptophan phenyl ester, and sarcosine phenyl ester.

Amides of amino acids which can be used in the process of the present invention include alaninamide, aspartic acid amide, aspartic acid diamide, glutamic acid amide, glutamic acid diamide, phenylalaninamide, glycinamide, histidinamide, isoleucinamide, lysinamide, leucinamide, methioninamide, asparaginamide, prolinamide, glutaminamide, argininamide, valinamide, tryptophanamide, sarcosinamide, and γ-aminobutyric acid amide.

Polyamines which can be used in the process of the present invention include histamine, dopamine, isophorone diamine, polylysine, polyhistidine, 1,2-diaminocyclohexane, ethylenediamine, diethylenetriamine, triethylenetetramine, tetraethylenepentamine, polyallylamine, tetramethylethylene diamine, polyvinylpyridine, pentaethylenehexamine, N,N-bis(3-aminopropyl)methylamine, 2-(diethylamino)ethylamine, 3-(diethylamino)propylamine, 3,3'-dimethyl-4,4'-diaminodicyclohexylmethane, 3-(dimethylamino)propylamine, iminobis propylamine, 3-(methylamino)propylamine, neopentanediamine, N,N,N',N,N-pentamethyldiethylenetriamine, 1,2-propylenediamine, N,N',N'-tetramethyl-1,6-hexanediamine, and 4,7,10-trioxatridecane-1,13-diamine.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

General procedure for preparing polycyanopolyphosphate mixtures from phosphoric anhydride and hydrocyanic acid and its salts as starting materials for reactions with primary and secondary amines Under an inert atmosphere, 1 molar part of $P_4O_{10}$ was mixed with dry $CH_3CN$ (4 mL per mmol $P_4O_{10}$) and a few molar parts (four parts preferred) of dry tertiary amine were added. The mixture was then heated at 30–40° C. to effect partial or total dissolution of $P_4O_{10}$ (about 5–10 min), after which several molar parts (four parts preferred) of dry liquid HCN or MCN (wherein M=K, Na, Li, etc.; KCN and NaCN should be powdered under an inert atmosphere) were added to this solution cooled in an ice bath with magnetic stirring. The mixture was heated at the specified temperature, usually between 30–80° C., for the specified time period, usually between 2–20 hr. In the reaction with HCN, at the end of the time period, the homogeneous solution was purged by nitrogen for 2 hr, and the purge stream directed through a series of basic bleach scrubbers. When KCN was used, the reaction mixture was heterogeneous.

Example 2

Preparation of Potassium Dicyanophosphinate

The reaction was carried out in acetonitrile (10 mL) with $P_4O_{10}$ (0.961 g, 3.39 mmol), triethylamine (1.36 g, 13.44 mmol), and $K^{13}CN$ (0.945 g, 14.3 mmol) at 50° C. for 16 hr. The acetonitrile solution containing the soluble product was separated from the precipitate. The solvent and amine were recovered under reduced pressure yielding 0.27 g (1.75 mmol) of the potassium salt of dicyanophosphonic acid, whose structure was established by X-ray analysis and NMR spectroscopy: $^{31}P$ NMR ($CH_3CN$) –52.4 ppm (t, $^1J_{PC}$=152.6 Hz), $^{13}C$ NMR ($CH_3CN$) 121.0 ppm (d, $^1J_{CP}$=152.6 Hz).

Example 3

Preparation of Dipotassium Dicyanopyrophosphonate

The reaction was carried out in acetonitrile (10 mL) with $P_4O_{10}$ (0.71 g, 2.25 mmol), triethylamine (1.01 g, 10 mmol), and $K^{13}CN$ (0.70 g, 10.6 mmol) at 50° C. for 16 hr. The precipitate was separated from the acetonitrile solution containing the soluble components. Then it was washed with three portions of DMF at room temperature to extract the dicyanopyrophosphonate salt. After precipitating with ether, 0.9 g of the solid product was obtained having one signal at –35 ppm in the $^{31}P$ NMR spectrum (DMF).

Preparation of Cyanoamidophosphonates

Example 4

Preparation of Potassium Isopropylamidocyanophosphonate

Under an inert atmosphere, 0.031 g (0.2 mmol) of potassium dicyanophosphinate from Example 2 was dissolved in 2 mL of dry DMF and 0.015 g (0.25 mmol) of isopropylamine was added. The solution was heated at 50° C. for 16 hr giving, according to the $^{31}P$ NMR spectrum (DMF), 36% dipotassium dicyanopyrophosphonate, –35.1 ppm (dt, $^1J_{CP}$= 180.1 Hz, $^3J_{CP}$=10.8 Hz) and 64% potassium isopropylamidocyanophosphonate, –19.6 ppm (dt, $^1J_{CP}$= 122.1 Hz, $J_{PH}$=9.2 Hz). After 3 days of heating at 50° C., the $^{31}P$ NMR spectrum showed the presence of only potassium isopropylamidocyanophosphonate.

Example 5

Preparation of Potassium Isopropylamidocyanophosphonate

Under an inert atmosphere, 0.031 g (0.2 mmol) of potassium dicyanophosphinate, obtained from the reaction of $P4O_{10}$, triethylamine, and a mixture of $K^{12}CN$ and $K^{13}CN$ (10:1), was dissolved in 5 mL of dry acetonitrile and 0.015 g (0.25 mmol) of isopropylamine was added. The solution was heated at 80° C. for 16 hr giving, according to the $^{31}P$ NMR spectrum ($CH_3CN$), potassium isopropylamidocyanophosphonate, –18.2 ppm (dt, $^1J_{CP}$= 131.2 Hz, $^3J_{PH}$=9.1 Hz). The $^{31}P$ NMR spectrum, recorded in $D_2O$ (the pH was adjusted to 2.0) after removing acetonitrile, showed a single signal at –15.4 ppm (dd, $^1J_{CP}$=141.9 Hz, $^3J_{PH}$=10.7 Hz).

Example 6

Preparation of Potassium Dimethylamidocyanophosphonate

Under an inert atmosphere, 0.031 g (0.2 mmol) of potassium dicyanophosphinate from Example 2 was dissolved in 2 mL of dry DMF, and 0.015 mL of a 2.0 M solution of dimethylamine in THF was added. The solution was heated at 50° C. for 16 hr in a closed vessel giving, according to the $^{31}P$ NMR spectrum (DMF), 33% dipotassium dicyanopyrophosphonate, –35.1 ppm (dt, $^1J_{CP}$=180.0 Hz, $^3J_{CP}$=10.7 Hz) and 67% potassium dimethylamidocyanophosphonate, –12.3 ppm (dm, $^1J_{CP}$= 111.0 Hz, $J_{PH}$=10.7 Hz).

Example 7

Preparation of Potassium Dibenzylamidocyanophosphonate Under an inert atmosphere, 0.20 g (1.30 mmol) of potassium dicyanophosphinate of Example 2 was dissolved in a mixture of dry DMF (1 mL) and dry $CH_3CN$ (2 mL), and 0.257 g (1.30 mmol) of dibenzylamine were added. The solution was heated at 30° C. for 16 hr giving, according to the $^{31}P$ NMR spectrum, 18% of starting material, –52.8 ppm (dt, $^1J_{CP}$=148.0 Hz), and 82% of the product, –16.4 ppm (d of quintets, $^1J_{CP}$=132.8 Hz, $^3J_{PH}$=10.7 Hz), $^{13}C$ NMR (DMSO-$d_6$) 121.7 ppm (d, $^1J_{CP}$=134.3 Hz). After additional heating at 80° C. for 4 hr the $^{31}P$ NMR spectrum showed the absence of starting material in the solution. The solvent was removed under reduced pressure, the solid residue was dissolved in dry $CH_3CN$ (10 mL) and was then precipitated with absolute ether, giving 0.22 g of the product (52% yield). Mass spectral analysis (FAB$^+$ TGL) detected peaks at m/z 364 and 688.8, respectively, corresponding to the complex species [[K$^+$–O[N(C$_7$H$_7$)$_2$]PO$^{13}$CN][K]$^+$] and [[K$^+$–O[N (C$_7$H$_7$)$_2$]PO$^{13}$CN]$_2$[K]$^+$], an anionic species (FAB$^-$, TGL) at m/z 286 [N$^{13}$CP(O)[N(C$_7$H$_7$)$_2$]O$^-$], and to the cluster [K$^+$O [N(C$_7$H$_7$)$_2$]PO$^{13}$CN$^-$]O(N(C$_7$H$_7$)$_2$PO$^{13}$CN]$^-$ at m/z 610.8. High resolution mass spectrum: observed mass, 286.0827. Calculated mass for [C$_{14}$H$_{14}$$^{13}$CPN$_2$O$_2$+H]$^+$, 286.0826.

Example 8

Preparation of Potassium Dibenzylamidocyanophosohonate

Under an inert atmosphere, 0.25 g (1.27 mmol) of dibenzylamine was added to the solution of the mixture of polycyanopolyphosphates in DMF (2 mL), obtained from $P_4O_{10}$ (0.07 g, 0.225 mmol), $K^{13}CN$ (0.066 g, 1 mmol) and 4-tert-butylpyridine (0.135 g, 1 mmol) in $CH_3CN$, at 40° C. for 16 hr, followed by removal of acetonitrile under reduced pressure. The DMF-dibenzylamine-containing reaction mixture was then heated at 40° C. for 16 hr. The $^{31}P$ NMR (DMF) spectrum shows a 43% yield of potassium dibenzylamidocyanophosphonate, –16.6 ppm (d of quintets, $^1J_{CP}$=141.9 Hz, $^3J_{PH}$=10.7 Hz).

Example 9

Preparation of Potassium Benzylamidocyanophosphonate

Under an inert atmosphere, 0.32 g (2.98 mmol) of benzylamine was added to the solution of the mixture of polycyanopolyphosphates in DMF (2 mL), obtained according to the procedure of Example 8 and heated at 45° C. for 72 hr. After the addition of $D_2O$ to the DMF solution (1:5), the $^{31}P$ NMR (DMF+$D_2O$) spectrum shows the presence of 14% potassium monobenzylamidocyanophosphonate: −17.5 ppm (dq, $^1J_{CP}$=140.3 Hz, $J_{PH}$=12.2 Hz).

Example 10

Preparation of Potassium N-methyl-N-phenylamidocyanophosphonate

Under an inert atmosphere, 0.32 g (2.98 mmol) of N-methylaniline was added to the solution of the mixture of polycyanopolyphosphates in DMF (2 mL), obtained according to the procedure of Example 8 and heated at 40° C. for 16 hr. After removing the DMF under reduced pressure, the residue was dissolved in $D_2O$. The $^{31}P$ NMR spectrum showed the presence of two new signals: −15.5 ppm (dq, $^1J_{CP}$=145.0 Hz, $^3J_{PH}$=10.7 Hz), corresponding to potassium N-methyl-N-phenylamidocyanophosphonate (NMR yield, 21%); −16.5 ppm (d, $^1J_{CP}$=145.0 Hz) monocyanophosphonate, NMR yield, 23%.

Example 11

Preparation of Diethylamidocyanophosphonate

Diethylamine (0.093 g, 1.27 mmol) was added to 1 mL of the acetonitrile solution of the mixture obtained by reaction of $P_4O_{10}$ (0.56 g, 1.97 mmol), $H^{13}CN$ (0.4 mL, 10 mmol), and N,N-tetramethylethylenediamine (0.92 g, 7.9 mmol) in 8 mL of $CH_3CN$, at 48° C. for 19 hr. The reaction mixture was heated at 40° C. for 24 hr to give a heterogenous mixture. After removing acetonitrile under reduced pressure and dissolving the residue in $D_2O$, the $^{31}P$ NMR ($D_2O$) spectrum showed the presence of two new signals corresponding to diethylamidocyanophosphonate (NMR yield, 20.5%) at −16.4 ppm (d of quintets, $^1J_{CP}$=131.2 Hz, $^3J_{PH}$=12.2 Hz), and monocyanophosphonate (NMR yield, 36.1%) at −18.8 ppm (d, $^1J_{CP}$=140.4 Hz).

Example 12

Preparation of Diethylamidocyanophosphonate

Diethylamine (0.050 g, 0.68 mmol) was added to 0.95 g of acetonitrile solution of the mixture obtained by reaction of $P_4O_{10}$ (0.85 g, 2.99 mmol), HCN, 10% enriched in $H^{13}CN$, (0.65 mL, 16.85 mmol), and quinuclidine (1.34 g, 12.1 mmol) in 12 mL of $CH_3CN$, at 48° C. for 19 hr (the total weight of the $P_4O_1$ mixture, including solvent, after nitrogen purging was 11.10 g). The reaction mixture was heated at 40° C. for 24 hr to give a heterogeneous mixture. The $^{31}P$ NMR ($CD_3CN$) of the soluble fraction in acetonitrile shows the presence of two new signals corresponding to diethylamidocyanophosphonate (NMR yield, 49.6%) at −18.0 ppm (quintet, $^3J_{PH}$=10.7 Hz; $^1J_{CP}$=131.2 Hz, measured on satellite peaks), and monocyanophosphonate (NMR yield, 6.7%) at −18.8 ppm (s; $^1J_{CP}$=138.8 Hz, measured on satellite peaks). The $^{31}P$ NMR (DMSO-$d_6$) spectrum of the insoluble fraction in acetonitrile shows the presence of only one signal corresponding to monocyanophosphonate at −18.4 ppm (s; $^1J_{CP}$=135.8 Hz, measured on satellite peaks).

Example 13

Preparation of Pyrrolidinocyanophosphonate

Pyrrolidine (0.070 g, 0.99 mmol) was added to 0.95 g of acetonitrile solution of the mixture obtained by reaction of $P_4O_{10}$ (0.85 g, 2.994 mmol), HCN enriched with 10% of $H^{13}CN$ (0.65 mL, 16.85 mmol), and quinuclidine (1.34 g, 12.1 mmol) in 12 mL of $CH_3CN$, at 48° C. for 19 hr (the total weight of the $P_4O_{10}$ reaction mixture, including solvent, after nitrogen purging was 11.10 g). The reaction mixture was heated at 40° C. for 3 hr to give a heterogeneous mixture. The $^{31}P$ NMR ($CD_3CN$) spectrum shows the presence of two new signals corresponding to pyrrolidinocyanophosphonate (NMR yield, 21.0%) at −15.2 ppm (quintet, $^3J_{PH}$=5.3 Hz; $^1J_{CP}$=120.6 Hz, measured on satellite peaks), and monocyanophosphonate (NMR yield, 26.3%) at −17.0 ppm (s; $^1J_{CP}$=135.8 Hz, measured on satellite peaks). The insoluble fraction in acetonitrile contains monocyanophosphonate.

Example 14

Preparation of Potassium Pyrrolidinocyanophosphonate

Under an inert atmosphere, 0.054 g (0.2 mmol) of dipotassium dicyanopyrophosphonate from Example 3 was dissolved in 2 mL of dry DMF and 0.014 g (0.2 mmol) of pyrrolidine was added. The solution was heated at 80° C. for 3 days giving a heterogeneous mixture, whose soluble part, according to the $^{31}P$ NMR spectrum (DMSO), contains 90% potassium pyrrolidinocyanophosphonate, −15.1 ppm (d of quintet, $^1J_{CP}$=106.8 Hz, $J_{PH}$=5.4 Hz). The insoluble fraction in DMF contains monocyanophosphonate.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A process for preparing a cyanophosphonamide comprising:
   first reacting phosphoric anhydride and a cyanide in a reaction to produce a cyanooxyphosphorus compound, and
   second reacting the cyanooxyphosphorus compound with an amino compound to produce the cyanophosphonamide.

2. The process of claim 1 wherein the cyanide is soluble in the reaction mixture.

3. The process of claim 1 wherein the cyanide is hydrogen cyanide, an alkali metal cyanide, an alkaline earth metal cyanide, a Group IB metal cyanide, an ammonium cyanide, a tetraalkyl ammonium cyanide, a tetraalkyl phosphonium cyanide, a trialkyl sulfonium cyanide, a cyanide of a cationic form of an organic amine or mixtures thereof.

4. The process of claim 1 wherein the cyanide is potassium cyanide, sodium cyanide, lithium cyanide, silver cyanide, gold cyanide, copper cyanide, tetrabutylammonium cyanide or mixtures thereof.

5. The process of claim 1 wherein the cyanide is potassium cyanide, sodium cyanide, tetrabutylammonium cyanide or mixtures thereof.

6. The process of claim 1 wherein the molar ratio of the cyanide to the phosphoric anhydride added is about 1 to about 15.

7. The process of claim 1 wherein the molar ratio of the cyanide to the phosphoric anhydride added is about 2 to about 10.

8. The process of claim 1 wherein the molar ratio of the cyanide to the phosphoric anhydride added is about 3.5 to about 8.5.

9. The process of claim 1 wherein the reaction of the phosphoric anhydride and the cyanide is performed at a temperature of about 0° C. to about 150° C.

10. The process of claim 9 wherein the temperature is about 30° C. to about 90° C.

11. The process of claim 1 wherein the reaction of the phosphoric anhydride and the cyanide is performed for a period of time of about 0.5 hours to about 50 hours.

12. The process of claim 11 wherein the period of time is about 1 hour to about 20 hours.

13. The process of claim 11 wherein the period of time is about 1 hour to about 6 hours.

14. The process of claim 1 wherein in at least one of the first reaction step and the second reaction step the reaction mixture further contains a solvent.

15. The process of claim 14 wherein in the second reaction step the solvent is an aprotic solvent.

16. The process of claim 15 wherein in the second reaction step the solvent is an aprotic polar solvent.

17. The process of claim 16 wherein in the second reaction step the solvent is selected from the group consisting of amides, ethers, sulfoxides, esters, and nitriles.

18. The process of claim 14 wherein in the first reaction step the solvent is acetonitrile, benzylcyanide, adiponitrile, propionitrile, dimethylacetonitrile, sulfolane, or mixtures thereof.

19. The process of claim 14 wherein in the first reaction step the solvent is acetonitrile, benzylcyanide, or adiponitrile.

20. The process of claim 1 wherein the reaction mixture further comprises a Lewis base.

21. The process of claim 20, wherein the Lewis base is a tertiary amine.

22. The process of claim 20 wherein the Lewis base is selected from the group consisting of triethylamine, tris[2-(2-methoxyethoxy)ethyl]amine, trimethylamine, 4-t-butylpyridine, quinuclidine, and mixtures thereof.

23. The process of claim 20 wherein the Lewis base is 4-t-butylpyridine or quinuclidine.

24. The process of claim 20 wherein the molar ratio of the Lewis base to the phosphoric anhydride added is about 1 to about 10.

25. The process of claim 20 wherein the molar ratio of the Lewis base to the phosphoric anhydride added is about 2 to about 8.

26. The process of claim 20 wherein the molar ratio of the Lewis base to the phosphoric anhydride added is about 3 to about 6.

27. The process of claim 1 wherein the cyanooxyphosphorus compound is a dicyanophosphinate, a cyanopolyphosphate, or a dicyanopolyphosphate.

28. The process of claim 1 wherein the amino compound is a primary or secondary amine, or a salt thereof.

29. The process of claim 1 wherein the amino compound is an aliphatic or aromatic primary amine.

30. The process of claim 1 wherein the amino compound is ammonia, isopropylamine, benzylamine or 4-(N,N-dimethylamino)phenylamine.

31. The process of claim 1 wherein the amino compound is an aliphatic or aromatic secondary amine.

32. The process of claim 1 wherein the amino compound is dibenzylamine.

33. The process of claim 1 wherein the amino compound is selected from the group consisting of natural and unnatural amino acids, amino acid salts, amino acid esters, and amino acid amides.

34. The process of claim 1 wherein the molar ratio of the amino compound to the cyanide is about 0.2 to about 20.

35. The process of claim 1 wherein the molar ratio of the amino compound to the cyanide is about 0.9 to about 5.

36. The process of claim 1 wherein the reaction of the amino compound and the cyanooxyphosphorus compound is performed at a temperature of about 0° C. to about 80° C.

37. The process of claim 36 wherein the temperature is about 20° C. to about 50° C.

38. The process of claim 1 wherein the reaction of the amino compound and the cyanooxyphosphorus compound is conducted for a period of time of about 1 hour to about 100 hours.

39. The process of claim 38 wherein the period of time is about 2 hours to about 20 hours.

40. A process for preparing a cyanophosphonamide, comprising:

providing a cyanooxyphosphorus compound; and, reacting the cyanooxyphosphorus compound with an amino compound to produce the cyanophosphonamide.

41. The process of claim 40, wherein the cyanooxyphosphorus compound is a cyanophosphonate or a salt thereof.

42. The process of claim 40, wherein, in the providing step, at least two cyanooxyphosphorus compounds are provided, and in the reacting step, the at least two cyanooxyphosphorus compounds are reacted with the amino compound.

43. The process of claim 40, wherein the cyanooxyphosphorus compound is a dicyanophosphinate.

44. The process of claim 40, wherein the cyanooxyphosphorus compound is a dicyanopyrophosphonate.

45. The process of claim 40, wherein the cyanooxyphosphorus compound is a dicyanotripolyphosphate.

46. The process of claim 40, wherein the cyanooxyphosphorus compound is a cyanopyrophosphate.

47. The process of claim 40, wherein the cyanooxyphosphorus compound is a cyanopolyphosphate.

48. The process of claim 40, wherein the cyanooxyphosphorus compound is a dicyanotetrapolyphosphate.

\* \* \* \* \*